US005695680A

United States Patent [19]

Weitzel et al.

[11] Patent Number: 5,695,680
[45] Date of Patent: Dec. 9, 1997

[54] LIQUID CRYSTALLINE DORISTEROL-CONTAINING ORGANOSILOXANES

[75] Inventors: Hans-Peter Weitzel, Reischach; Franz-Heinrich Kreuzer, Martinsried; Robert Maurer, München, all of Germany

[73] Assignee: Consortium für elektrochemische Industrie GmbH, Munich, Germany

[21] Appl. No.: 406,978

[22] PCT Filed: Oct. 14, 1993

[86] PCT No.: PCT/EP93/02842

§ 371 Date: Apr. 3, 1995

§ 102(e) Date: Apr. 3, 1995

[87] PCT Pub. No.: WO94/09086

PCT Pub. Date: Apr. 28, 1994

[30] Foreign Application Priority Data

Oct. 15, 1992 [DE] Germany ............. 42 34 845.5

[51] Int. Cl.$^6$ ............. C09K 19/52; G02F 1/13; C07F 7/08
[52] U.S. Cl. ............. 252/299.01; 252/299.62; 252/299.63; 252/299.64; 252/299.66; 349/104; 428/1; 556/445
[58] Field of Search ............. 252/299.01, 299.61, 252/299.62, 299.64, 299.66; 428/1; 349/104; 556/445

[56] References Cited

U.S. PATENT DOCUMENTS

| 3,888,892 | 6/1975 | Leder ............. 252/299.01 |
| 3,888,992 | 6/1975 | Leder ............. 252/299.01 |
| 3,907,406 | 9/1975 | Leder ............. 252/299.01 |
| 4,388,453 | 6/1983 | Finkelmann et al. ............. 528/15 |
| 4,410,570 | 10/1983 | Kreuzer et al. ............. 252/299.01 |
| 5,066,107 | 11/1991 | Yoshinaga et al. ............. 359/103 |
| 5,211,877 | 5/1993 | Andreiewske et al. ............. 252/299.01 |
| 5,221,759 | 6/1993 | Häberle et al. ............. 556/413 |
| 5,304,667 | 4/1994 | Häberle et al. ............. 556/413 |
| 5,605,649 | 2/1997 | Stohrer et al. ............. 252/299.01 |

FOREIGN PATENT DOCUMENTS

| 0466183 | 1/1992 | European Pat. Off. . |
| 0358208 | 3/1994 | European Pat. Off. . |

OTHER PUBLICATIONS

"Hydrolytic Processes" in Chemistry and Technology of Silicones, pp. 191–239 by Walter Noll, 1969.

"Optical notch filter using thermotropic liquid crystalline polymers" by M.L. Tsai et al., American Institute of Physics, 1989, pp. 2395–2397.

"Nematic liquid single crystal elastomers" by J. Küpfer et al., Makromol. Chem., Rapid Commun, 12, pp. 717–726 (1991).

*Primary Examiner*—Shean C. Wu
*Attorney, Agent, or Firm*—Martin Connaughton

[57] ABSTRACT

The liquid crystalline organosiloxanes contain per molecule at least one doristeryl group bonded at the 3β position and can be used as right-handed filter materials and optical media.

5 Claims, No Drawings

LIQUID CRYSTALLINE DORISTEROL-CONTAINING ORGANOSILOXANES

This application is a 371 of PCT/EP 93/02842 filed on Oct. 14, 1993.

The present invention relates to liquid crystalline organosiloxanes containing doristeryl radicals, a process for their preparation, their use, organosilanes which can be condensed to give organosiloxanes containing liquid crystalline doristeryl radicals and mixtures of doristerol-containing organosiloxanes with other liquid crystalline materials.

For some optical applications of liquid crystalline materials, such as e.g. in notch filters, it is necessary to have cholesteric phases having a right-handed helix and cholesteric phases having a left-handed helix in order to be able to reflect both left and right circularly polarized light.

For left-handed helical filters, resort is frequently made here of cholesterol compounds, i.e. steroid compounds, which apart from the chirality have an adequate mesogenicity, i.e. an adequate tendency to form liquid crystalline phases to produce a stable mesophase. The cyclic organosiloxanes containing cholesteryl radicals disclosed in U.S. Pat. No. 4,410,570 are suitable, for example, for this.

In the production of right-handed helical filters, use was until now made of nonsteroidal molecules which have various disadvantages.

From M. L. Tsai, S. H. Chen, S. D. Jacobs, Appl. Phys. Lett., 54, 2395, 1989, it is known that modified hydroxypropylcellulose does not have adequate mesophase stability and polybenzyl glutamates have too low a glass transition point of −25° C. for long-term stability.

The only known sterol whose esters yield a right-handed helix is the cholest-8(14)-en-3β-ol described in U.S. Pat. No. 3,907,406 and U.S. Pat. No. 3,888,892, of the formula 1

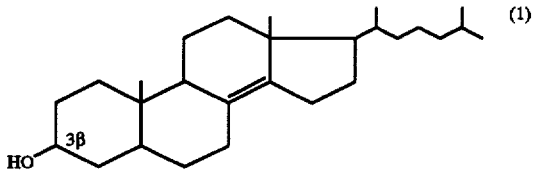

(1)

abbreviated as doristerol in the following. The compounds described are aliphatic esters, halo or carbonate derivatives of doristerol which on the one hand only have small mesophase widths and on the other hand can only be used at elevated temperature on account of the crystalline state at room temperature.

The object of the present invention was to make available right-handed helical liquid crystalline materials which at room temperature have a stable cholesteric phase, make possible a selective reflection of right-handed polarized light and whose reflection wavelength is largely temperature-independent. This material should additionally have a helical twisting power (htp) which is as high as possible, i.e. a high tendency to form helical screw structures, in order to be able to keep the proportion of the expensive chiral component low.

The abovementioned objects are achieved by the present invention by means of liquid crystalline organosiloxanes which, per molecule, contain at least one doristeryl radical bonded via the 3β-position.

The liquid crystalline organosiloxanes according to the invention show a low tendency towards crystallization, a stabilization and broadening of the cholesteric phase compared with the known doristerol derivatives and are present in the glass state at room temperature.

The cholesteric phase can be preserved in the glass state by quenching after alignment above the glass transition temperature and is stable at room temperature. The higher glass transition points of the liquid crystalline organosiloxanes according to the invention in comparison with known right-handed helical materials produce a higher stability in the frozen cholesteric phase at room temperature.

The liquid crystalline organosiloxanes according to the invention have distinctly wider mesophases than the known low molecular weight doristeryl compounds. For example, the average values in the liquid crystalline cyclic organosiloxanes according to the invention are about g30*130i, while doristeryl propionate, for example, has values of k80, 5n*83, 5i and doristeryl benzoate values of k111n*140.5i.

The liquid crystalline organosiloxanes according to the invention have a distinctly greater htp and thus a better optical power of rotation per doristeryl radical than the low molecular weight doristeryl derivatives, such that to achieve the same optical effect smaller amounts of doristerol compound have to be employed. The cyclic organosiloxanes containing cholesteryl radicals described in U.S. Pat. No. 4,410,570 do not show a greater htp in comparison to the corresponding low molecular weight cholesterol compounds.

Besides the doristeryl radicals, the liquid crystalline organosiloxanes preferably contain still other mesogenic radicals which make possible the subsequent free radical or ionic crosslinking of the right-handed helical filter.

By altering the content of doristeryl radicals and the ratio of doristeryl radicals to other mesogenic radicals in the liquid crystalline organosiloxanes according to the invention, the reflection wavelength of the selective reflection can be adjusted. On account of the high htp values, only an amount of 10 to 20 mol %, based on all mesogenic radicals present in the organosiloxanes on doristeryl radicals, is required in order to obtain a reflection in the visible range, while with the corresponding cholesterol-containing organosiloxanes between 40 and 50 mol % of cholesteryl radicals are required.

The doristeryl radicals are preferably bonded to the siloxane structure via other mesogenic groups. The term "mesogenic groups" is well known in the field. These are those groups which can produce liquid crystalline properties in a molecule.

Examples of mesogenic groups are derivatives of cyclohexane, such as cyclohexyl cyclohexylcarboxylates, phenyl cyclohexylcarboxylates, cyclohexylbenzenes, dicyclohexyl derivatives, derivatives of stilbene, phenyl benzoate and its derivatives, steroids, such as cholesterol, its derivatives, such as cholesterol esters, cholestane and its derivatives, benzylideneanilines, azobenzene and its derivatives, azoxybenzene and its derivatives, alkyl and alkoxyderivatives of biphenyl and Schiff's bases.

It is often desired for application technology reasons that the mesogenic groups contain polar functions, such as, for example, the nitrile group, in order to achieve a high dielectric anisotropic effect in the liquid crystal.

The abovementioned liquid crystalline organosiloxanes are preferably those which are constructed from at least two units of the general formula 2

(2), in which B is a mesogenic radical of the general formula 3

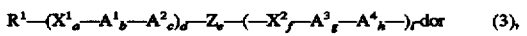
(3), and optionally a mesogenic radical of the general formula 4

$$R^1-(X^1{}_a-A^1{}_b-A^2{}_c)_d-Z_e-(-X^2{}_f-A^3{}_g-A^4{}_h-)_i-A^5{}_k \quad (4),$$

where in the above formulae 2, 3 and 4

R is identical or different, optionally substituted $C_1$- to $C_{18}$-hydrocarbon radicals, o is an integer of value 0 to 3, p is an integer of value 0 to 3 and an average value of 0.8 to 2.2, q is an integer of value 0 to 3 and the sum of o, p and q is at most 3, $R^1$ is a radical of the formula $C_nH_m$ in which n is an integer of value 1 to 20, m has the value 2n, or if n is at least 2, can also have the value (2n–2), and in $R^1$ one or more methylene units can be replaced by oxygen atoms which can be bonded to carbon and/or silicon atoms, $X^1$ and $X^2$ are identical or different bivalent radicals from the group consisting of —O—, —COO—, —CONH—, —CO—, —S—, —C≡C—, —CH=CH—, —CH=N—, —CH$_2$CH$_2$—, —N=N— and —N=N(O)—, $A^1$, $A^2$, $A^3$ and $A^4$ are identical or different bivalent radicals, namely 1,4-phenylene or 1,4-cyclohexylene radicals, substituted arylenes having 6 to 10 carbon atoms, substituted cycloalkylenes having 6 to 10 carbon atoms and heteroarylenes having 1 to 10 carbon atoms, Z is identical or different bi- or tetravalent benzene, cyclohexane or cyclopentane radicals, dor is a doristeryl radical bonded via the 3β-position, $A^5$ is identical or different, saturated or olefinically unsaturated alkyl, alkoxy or cycloalkyl radicals in each case having 1 to 16 carbon atoms, cholestane radicals, cholesteryl radicals, halogen atoms, hydrogen atoms, hydroxyl, nitrile, acryloxy, (meth)acryloxy, (meth)acryloxyethylenoxy, (meth)acryloxydi(ethylenoxy), (meth)acryloxytri(ethylenoxy) and trialkylsiloxy groups whose alkyl radicals in each case have 1 to 8 carbon atoms, a, b, c, d, f, g, h, i and k in each case are identical or different integers of value 0 to 3, the sum a+b+c+d+e+f+g+h+i+k being at least 2 and the sum of d and i being at most 4, and e is an integer of value 0 or 1.

Examples of unsubstituted radicals R are alkyl radicals, such as the methyl, ethyl, n-propyl, isopropyl, n-butyl, isobutyl, tert-butyl, n-pentyl, isopentyl, neopentyl or tert-pentyl radical, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, octadecyl radicals, such as the n-octadecyl radical; alkenyl radicals, such as the vinyl radical and the allyl radical; cycloalkyl radicals, such as cyclopentyl, cyclohexyl or cycloheptyl radicals and methylcyclohexyl radicals; aryl radicals, such as the phenyl, naphthyl, anthryl and phenanthryl radicals; alkaryl radicals, such as o-, m- or p-tolyl radicals, xylyl radicals and ethylphenyl radicals; aralkyl radicals, such as the benzyl radical, the α- and the β-phenylethyl radical;

Examples of substituted radicals R are cyanoalkyl radicals, such as the β-cyanoethyl radical, and halogenated hydrocarbon radicals, for example haloalkyl radicals, such as the 3,3,3-trifluoro-n-propyl radical, the 2,2,2,2',2',2'-hexafluoroisopropyl radical and the heptafluoroisopropyl radical, and haloaryl radicals, such as the o-, m- and p-chlorophenyl radical. R in each case is preferably an optionally halogenated hydrocarbon radical having 1 to 18, in particular 1 to 10, carbon atoms.

Radicals R which are particularly preferred are $C_1$- to $C_4$-alkyl radicals and phenyl radicals, in particular methyl radicals.

The radicals $X^1$ and $X^2$, if they are not symmetrically constructed, can be bonded to each of their binding partners by each of their ends. Thus, for example, in the above formulae 3 and 4 and in the formulae below the radical —COO— can also be bonded as —OOC—, the radical —CONH— can also be bonded as —NHCO—, and —CH=N— can also be bonded as —N=CH—.

Substituents which are preferred for the substituted arylenes and cycloalkylenes $A^1$, $A^2$, $A^3$ and $A^4$ are halogen atoms, $C_1$- to $C_4$-alkoxy radicals, nitro and cyano groups, $C_1$- to $C_6$-alkyl radicals, carboxy-($C_1$- to $C_4$-alkyl) radicals and tri-($C_1$- to $C_4$-alkyl)-siloxy radicals.

Preferably, n in $R^1$ has a value of 3 to 6 and m preferably has the value 2n.

Examples of radicals $A^5$ are alkyl radicals, such as the methyl, ethyl, n-propyl, isopropyl, n-butyl, isobutyl, tert-butyl, n-pentyl, isopentyl, neopentyl or tert-pentyl radical, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, hexadecyl radicals, such as the n-hexadecyl radical; alkenyl radicals, such as the vinyl and the allyl radicals, butenyl, pentenyl, hexenyl, heptenyl, octenyl, octadienyl, decenyl, dodecenyl and hexadecenyl radicals; cycloalkyl radicals, such as cyclopentyl, cyclohexyl or cycloheptyl radicals and methylcyclohexyl radicals; alkoxy radicals, such as the methoxy, ethoxy, n-propoxy, isopropoxy, n-, sec- and tert-butoxyradicals, pentoxy, hexoxy, octoxy, decoxy- and hexadecoxy radicals; alkenoxy radicals, such as the allyloxy radical, butenyloxy, pentenyloxy, hexenyloxy, octenyioxy, decenyloxy and hexadecenyloxy radicals; cycloalkyl radicals, such as the cyclopentyl, cyclohexyl or cycloheptyl, radical; cycloalkenyl radicals, such as cyclopentenyl, cyclohexenyl and cycloheptenyl radicals; cholestane radicals; the cholesteryl radical; fluorine, chlorine or bromine atoms; hydrogen atoms; hydroxyl, nitrile and trimethylsilyl or triethylsilyl groups. It is very particularly preferred that —$R^1$—($X^1{}_a$—$A^1{}_b$—$A^2{}_c)_d$— in the abovementioned formulae 3 and 4 is a radical of the formula 11

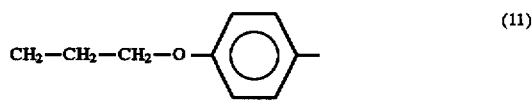
(11)

Radicals of the formulae 3 and 4 which are particularly preferred are those of the general formulae 12 and 13

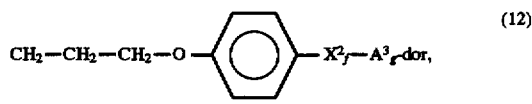
(12)

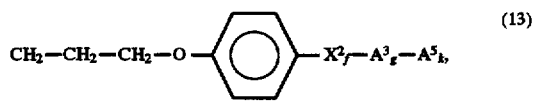
(13)

in which $X^2$, $A^3$, $A^5$, f, g and k have the meanings indicated for formulae 3 and 4 and f preferably has the value 1, g either 0 or 1 and k the value 1.

The liquid crystalline organosiloxanes according to the invention can be prepared by reaction of organosiloxanes and/or organosilanes which can be condensed to give organosiloxanes with alkenes or alkynes containing mesogenic groups, the organosiloxanes and at least some of the organosilanes having at least one hydrogen atom bonded directly to silicon.

In a preferred process for the preparation of liquid crystalline organosiloxanes of the above general formula 2, in which n in the mesogenic radicals of the general formulae 3 and 4 is an integer of value 2 to 20, organosiloxanes which are constructed from units of the general formula 14

 (14)

and/or organosilanes of the general formula 15

 (15)

are reacted with mesogenic compounds of the general formula 16

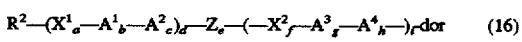 (16)

and optionally mesogenic compounds of the general formula 17

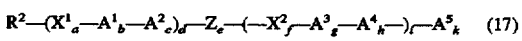 (17)

and, if organosilanes of the general formula 15 are employed, the organosilanes obtained of the general formula 18

 (18)

are condensed,
where in the above formulae 14 to 18
Y is a condensable group,
$R^2$ is a radical of the formula $C_nH_m$, in which
m has the value $2n-1$ or $2n-3$,
r and s in each case are an integer of value 0 to 3, the sum of o, r and s is at most 3, and o, p, q, $X^1$, $X^2$, $A^1$, $A^2$, $A^3$, $A^4$, $A^5$, a, b, c, d, e, f, g, h, i, k, Z, dor, B and R have the meaning indicated for the general formulae 2, 3 and 4.

Y is preferably a halogen atom or a $C_1$- to $C_4$-alkoxy group, in particular a chlorine atom or a methoxy or ethoxy group. The value of s is preferably 0 or 1.

In the above general formulae 16 and 17, n in $R^2$ preferably has a value of 3 to 6 and m preferably has the value $2n-1$.

The reaction of organosiloxanes containing hydrogen atoms bonded directly to silicon and/or organosilanes which can be condensed to give organosiloxanes with alkenes or alkynes containing mesogenic groups is carried out in a manner known per se, e.g. by hydrosilylation in solvents, such as hydrocarbons, ethers or esters using metals or compounds of the platinum group as catalyst. Suitable processes for hydrosilylation are described, for example, in EP-A-466 183 and in J. Küpfer, H. Finkelmann; Makromol. Chem., Rapid Commun. 12,717, 1991.

For the preparation of liquid crystalline organosiloxanes according to the invention which contain 4 methacryloxy and/or acryloxy groups in the mesogenic radicals of the general formula 4, the process described in EP-A-358 208 is preferred.

0.1 to 10 mol, in particular 0.5 to 2 mol, of compounds of the formulae 3 and 4 are preferably employed per gram atom of hydrogen atoms bonded directly to silicon atoms in the hydrosilylation.

Siloxanes of the formula (14) which are particularly preferred are those which are constructed to at least 90% of their units from those of the formulae 5 to 10

 (5)

 (6)

 (7)

 (8)

 (9)

and

 (10)

and contain 2 to 100 silicon atoms per molecule, in particular 2 to 15 silicon atoms per molecule.

If, in the process described above, organosilanes, for example of the general formula 15, are employed, these are condensed together with organosilanes or organosiloxanes containing doristeryl radicals to give liquid crystalline organosiloxanes by processes known per se. This can be carried out, inter alia, by reaction with acids, such as aqueous hydrochloric acid. Processes of this type are described in W. Noll: Chemistry and Technology of Silicones, Academic Press, Orlando Fla., 1968, page 191 to 239.

A mixture of different molecules is obtained by means of the reactions described above.

The novel organosilanes of the above general formula 18, in which o denotes an integer of value 1, 2 or 3, are likewise the subject of the present invention as intermediates for the preparation of the liquid crystalline organosiloxanes.

The doristerol-containing organosiloxanes according to the invention can be used in various ways in optical elements and as polarizing color filters, in particular notch filters. They allow the right-handed polarized portion of the light to be reflected in certain prespecified spectral ranges.

Both mixtures of the organosiloxanes according to the invention with one another and mixtures of the organosiloxanes according to the invention with other liquid crystalline materials or pure doristerol-containing organosiloxanes can be used for the above application. In particular, mixtures with other liquid crystalline substances, specifically also with left-handed helical materials, can also be used, by means of which a tuning of the reflection wavelength between 400 nm right-handed helical through infrared right-handed helical, nematic (=infinite pitch), infrared left-handed helical to 400 nm left-handed helical can be carried out.

The mixtures of the liquid crystalline organosiloxanes with one another and with other liquid crystalline materials are likewise a subject of the present invention.

The liquid crystalline organosiloxanes according to the invention, which have methacryloxy and/or acryloxy groups in the mesogenic radicals of the general formula 4, can be three-dimensionally crosslinked. This crosslinking is preferably effected by means of free radicals, which are produced by peroxides, by UV light or by more energy-rich electromagnetic radiation than UV light, or thermally. The crosslinking, however, can also be effected by means of crosslinkers containing hydrogen atoms bonded directly to silicon atoms with catalysis by the abovementioned platinum metal catalysts. It can also be carried out cationically or anionically. Crosslinking by UV light is particularly preferred. This crosslinking is described in EP-A-358 208.

In the following examples, if not indicated otherwise in each case, a) all quantitative data are based on the weight;
b) all pressures are 0.10 MPa (abs.);
c) all temperatures are 20° C.;
d) htp=helical twisting power;
e) n*=cholesteric;
f) g=glass;
g) k=crystalline;
h) i=isotropic.

EXAMPLE 1 a) Preparation of doristeryl 4-(propen-2-oxy)benzoate 50 g of cholestadiene were dissolved in 800 ml of dry ethyl acetate to which 30 ml of acetic acid had previously been added and after addition of 1.5 g of platinum oxide the mixture was transferred to an autoclave of 2 l volume. Hydrogenation was carried out at 50° C. and 10 atm hydrogen pressure and was complete after 24 h. After reaction was complete, the catalyst was filtered off, the solvent was concentrated in a rotary evaporator and the doristerol obtained was recrystallized from ethanol. Yield: 42.5 g (88.5%). The purity of the substance was confirmed with the aid of $^1$H-NMR and $^{13}$C-NMR spectroscopy. 17 g of 4-(propen-2-oxy)benzoyl chloride and 32 g of doristerol were dissolved in 200 ml of dry toluene and heated to reflux for 15 h. The solvent was then distilled off and the residue was recrystallized from ethanol; yield: 44.9 g (99%), m.p. 92° C. (n*105i).

b) Hydrosilylation 1 g of doristeryl 4-(propen-2-oxy)benzoate, 1.53 g of 4'-phenylphenyl 4-(propen-2-oxy)benzoate and 646 mg of pentamethylcyclopentasiloxane were dissolved in 20 ml of dry toluene and, after addition of 0.1 ml of a solution of dicyclopentadienylplatinumdichloride (1% by weight in methylene chloride), heated at 100° C. for 1 h. 1.45 g of (4-methacryloxy)phenyl 4-(propen-2-oxy)benzoate, 500 ppm of hydroquinone and a further 0.1 ml of the catalyst solution were added to the solution cooled to 50° C.; this solution was stirred at 70°–80° C. for half an hour. After reaction was complete, the catalyst was removed by means of a short column packed with silica gel (l=3 cm, diameter=3 cm) and the product was precipitated in ethanol. 2.8 g (60%) of a substance having a reflection wavelength of 456 nm—corresponding to an htp of 15.7 $\mu m^{-1}$—were obtained. The substance had a glass transition point at 27° C. and a clear point at 126° C.

EXAMPLE 2

1 g of doristeryl 4-(propen-2-oxy)benzoate, 1.81 g of 4'-phenylphenyl 4-(propen-2-oxy)benzoate and 733 mg of pentamethylcyclopentasiloxane were dissolved in 20 ml of dry toluene and, after addition of 0.1 ml of a solution of dicyclopentadienylplatinum dichloride (1% by weight in methylene chloride), the mixture was heated at 100° C. for 1 h. 1.65 g of (4-methacryloxy)phenyl 4-(propen-2-oxy) benzoate, 500 ppm of hydroquinone and a further 0.1 ml of the catalyst solution were added to the solution cooled to 50° C.; this solution was stirred at 70°–80° C. for half an hour. After reaction was complete, the catalyst was removed by means of a short column packed with silica gel (l=3 cm, diameter=3 cm) and the product was precipitated in ethanol. 2.4 g (46%) of a substance having a reflection wavelength of 500 nm—corresponding to an htp of 16.1 $\mu m^{-1}$—were obtained. The substance had a glass transition point at 31° C. and a clear point at 136° C.

EXAMPLE 3

1 g of doristeryl 4-(propen-2-oxy)benzoate, 2.69 g of 4'-phenylphenyl 4-(propen-2-oxy)benzoate and 1 g of pentamethylcyclopentasiloxane were dissolved in 20 ml of dry toluene and, after addition of 0.1 ml of a solution of dicyclopentadienylplatinum dichloride (1% by weight in methylene chloride), the mixture was heated at 100° C. for 1 h. 2.25 g of (4-methacryloxy)phenyl 4-(propen-2-oxy) benzoate, 500 ppm of hydroquinone and a further 0.1 ml of the catalyst solution were added to the solution cooled to 50° C.; this solution was stirred at 70°–80° C. for half an hour. After reaction was complete, the catalyst was removed by means of a short column packed with silica gel (l=3 cm, diemeter=3 cm) and the product was precipitated in ethanol. 3.8 g (55%) of a substance having a reflection wavelength of 681 nm—corresponding to an htp of 15.8 $\mu m^{-1}$—were obtained. The substance has a glass transition point at 23° C. and a clear point at 122° C.

EXAMPLE 4 a) Doristeryl 2-(propen-2-oxy)-6-naphthalenecarboxylate 3.2 g of 2-(propen-2-oxy)-6-naphthalenecarboxyl chloride and 5 g of doristerol were dissolved in 40 ml of dry toluene and heated to reflux for 6 h. The crude product was concentrated in a rotary evaporator and recrystallized from ethanol; yield 5.6 g (73%), m.p. 105° C. (n*132i).

b) Hydrosilylation 2 g of doristeryl 2-(propen-2-oxy)-6-naphthalenecarboxylate, 2.22 g of 4'-phenylphenyl 4-(propen-2-oxy)benzoate and 1 g of pentamethylcyclopentasiloxane were dissolved in 20 ml of dry toluene and, after addition of 0.1 ml of a solution of dicyclopentadienyl-platinum dichloride (1% by weight in methylene chloride), the mixture was heated at 100° C. for 1 h. 2.27 g of (4-methacryloxy)phenyl 4-(propen-2-oxy)benzoate, 500 ppm of hydroquinone and a further 0.1 ml of the catalyst solution were added to the solution cooled to 50° C.; this solution was stirred at 70°–80° C. for half an hour. After reaction was complete, the catalyst was removed by means of a short column packed with silica gel (l=3 cm, diameter=3 cm) and the product was precipitated in ethanol. 4.9 g (65%) of a substance having a reflection wavelength of 522 nm—corresponding to an htp of 13.4 $\mu m^{-1}$—were obtained. The substance had a glass transition point at 53° C. and a clear point at 147° C.

EXAMPLE 5

The doristerol-containing organosiloxane having a reflection wavelength of 456 nm prepared according to Example 1 was mixed in certain weight ratios with an appropriate cholesterol-containing organosiloxane having a reflection wavelength of 555 nm. The proportions by weight and reflection wavelengths of the mixtures are to be taken from the following table.

TABLE 1

| Doristerol-containing siloxane/% by weight | Cholesterol-containing siloxane/% by weight | Reflection wavelength/nm | Handedness of the helix r/l |
|---|---|---|---|
| 100 | 0 | 456 | r |
| 96.1 | 3.9 | 506 | r |
| 88.8 | 11.2 | 628 | r |
| 77.6 | 22.4 | 884 | r |
| 64.3 | 35.7 | 1891 | r |
| 34.5 | 65.5 | 1310 | l |
| 21.9 | 78.1 | 838 | l |
| 13.1 | 86.9 | 683 | l |

TABLE 1-continued

| Doristerol-containing siloxane/% by weight | Cholesterol-containing siloxane/% by weight | Reflection wavelength/nm | Handedness of the helix r/l |
|---|---|---|---|
| 4.1 | 95.9 | 583 | 1 |
| 0 | 100 | 555 | 1 |

Comparison Example 6

The htp values of low molecular weight doristerol compounds were measured by admixing in Merck-Nematen® ZLI-1565 and measuring the Grandjean-Cano disclination lines in a wedge cell. Doristerol has an htp of 8–9 µm$^{-1}$, doristeryl 4-(propen-2-oxy)benzoate an htp of 5 µm$^{-1}$.

We claim:

1. A liquid crystalline organosiloxane which contains at least one doristeryl radical bonded via the 3β-position per molecule comprising at least two units of the general formula 2

$$[B_oR_pH_qSiO_{(4-o-p-q)/2}] \quad (2),$$

in which B is a mesogenic radical of the general formula 3

  (3), and optionally a mesogenic radical of the general formula 4

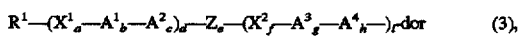  (4), where in the above formulae 2, 3 and 4

R is an identical or different, optionally substituted C$_1$- to C$_{18}$-hydrocarbon radical, o is an integer of value 0 to 3, p is an integer of value 0 to 3 q is an integer of value 0 to 3 and the sum of o, p and q is at most 3,

R$^1$ is a radical of the formula C$_n$H$_m$ in which n is an integer of value 2 to 20, m has the value 2n, or if n is at least 2, can also have the value (2n–2), and in R$^1$ one or more methylene units can be replaced by oxygen atoms which can be bonded to carbon and/or silicon atoms, X$^1$ and X$^2$ are identical or different bivalent radicals from the group consisting of —O—, —COO—, —CONH—, —CO—, —S—, —C≡C—, —CH=CH—, —CH=N—, CH$_2$CH$_2$—, —N=N— and —N=N(O)—, A$^1$, A$^2$, A$^3$ and A$^4$ are identical or different bivalent radicals, selected from the group consisting of 1,4-phenyllene or 1,4-cyclohexylene radicals, substituted arylenes having 6 to 10 carbon atoms, and substituted cycloalkylenes having 6 to 10 carbon atoms, Z is identical or different bi- or tetravalent benzene, cyclohexane or cyclopentane radicals, dor is a doristeryl radical bonded via the 3β-position, A$^5$ is identical or different, saturated or olefinically unsaturated alkyl, alkoxy or cycloalkyl radicals in each case having 1 to 16 carbon atoms, cholestane radicals, cholesteryl radicals, halogen atoms, hydrogen atoms, hydroxyl, nitrile, acryloxy, (meth)acryloxy, (meth)acryloxyethylenoxy, (meth)acryloxydi(ethylenoxy), (meth)acryloxytri(ethylenoxy) and trialkylsiloxy groups whose alkyl radicals in each case have 1 to 8 carbon atoms, a, b, c, d, f, g, h, i and k in each case are identical or different integers of value 0 to 3, the sum a+b+c+d+e+f+g+h+i+k being at least 2 and the sum of d and i being at most 4, and e is an integer of value 0 or 1.

2. A process for the preparation of liquid crystalline organosiloxanes as claimed in claim 1, in which n in the mesogenic radicals of formulae 3 and 4 is an integer of value 2 to 20, which comprises reacting organosiloxanes comprising units of the formula

  (14)

and/or organosilanes of the formula

  (15)

with mesogenic compounds of the formula

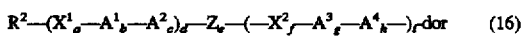  (16)

and optionally mesogenic compounds of the formula

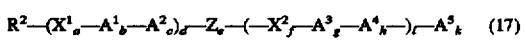  (17)

and, if organosilanes of formula 15 are present, condensing the organosilanes obtained of the formula

  (18)

where in the above formulae 14 to 18

Y is a condensable group,

R$^2$ is a radical of the formula C$_n$H$_m$, in which m has the value 2n–1 or 2n–3, r and s are an integer of value 0 to 3, the sum of o, r and s is at most 3, and o, p, q, X$^1$, X$^2$, A$^1$, A$^2$, A$^3$, A$^4$, A$^5$, a, b, c, d, e, f, g, h, i, k, Z, dor, B and R have the meaning indicated in claim 1.

3. A liquid crystalline organosiloxane as claimed in claim 1 comprising a mixture of a liquid crystalline organosiloxane having at least one doristeryl radical bonded via the 3β-position and other liquid crystalline materials and optionally left-handed helical cholesteric materials.

4. A process for the preparation of liquid crystalline organosiloxanes as claimed in claim 2 containing organosilanes of the general formula 18, where o is an integer having a value of 1, 2 or 3.

5. An optical filter material containing a liquid crystalline organosiloxane as claimed in claim 1.

* * * * *